US009609858B2

(12) United States Patent
Stowe et al.

(10) Patent No.: US 9,609,858 B2
(45) Date of Patent: Apr. 4, 2017

(54) UNWANTED PLANT REMOVAL SYSTEM HAVING VARIABLE OPTICS

(71) Applicant: Palo Alto Research Center Incorporated, Palo Alto, CA (US)

(72) Inventors: Timothy David Stowe, Alameda, CA (US); Patrick Yasuo Maeda, San Jose, CA (US); Tim Curley, San Carlos, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 479 days.

(21) Appl. No.: 14/027,117

(22) Filed: Sep. 13, 2013

(65) Prior Publication Data

US 2015/0075066 A1  Mar. 19, 2015

(51) Int. Cl.
*A01M 21/04* (2006.01)
*A01M 21/00* (2006.01)
(Continued)

(52) U.S. Cl.
CPC ......... *A01M 21/046* (2013.01); *A01D 34/015* (2013.01); *A01D 34/835* (2013.01);
(Continued)

(58) Field of Classification Search
CPC ... A01M 21/046; A01D 34/00; A01D 34/006; A01D 34/015; A01D 34/01; A01D 34/06
USPC .......... 47/1.01 R, 1.3, 1.43, 58.1 R, 58.1 LS; 362/259, 553; 372/9, 26, 50.11, 50.12, 372/50.122; 330/4.3, 7.51; 359/563
See application file for complete search history.

(56) References Cited

U.S. PATENT DOCUMENTS 3,652,844 A  3/1972 Scott, Jr.
5,220,307 A  6/1993 May et al.
(Continued)

FOREIGN PATENT DOCUMENTS

DE  4039797 A1  9/1991
DE  4339329  5/1996
(Continued)

OTHER PUBLICATIONS

Feb. 3, 2016, File History for U.S. Appl. No. 14/027,116.
(Continued)

*Primary Examiner* — Danielle Clerkley
(74) *Attorney, Agent, or Firm* — Hollingsworth Davis, LLC

(57) ABSTRACT

Embodiments of an apparatus and methods can removing unwanted plants or weeds from an area such as an agricultural plot or lawn. The apparatus includes a three-dimensional imager configured to capture plant images and locate plants; an image processor configured to distinguish between wanted and unwanted plants based upon the captured plant images; at least one laser device configured to emit a laser beam having power sufficient to damage the unwanted plants; a guidance system configured to direct at least one laser beam toward the unwanted plant; and a chassis configured to support the three-dimensional imager, the laser device, and the guidance system. The chassis is configured to be moved across the area.

10 Claims, 14 Drawing Sheets

(51) Int. Cl.
*A01D 34/01* (2006.01)
*A01D 34/835* (2006.01)
*G01N 21/29* (2006.01)
*G01N 21/84* (2006.01)

(52) U.S. Cl.
CPC ............ *A01M 21/00* (2013.01); *G01N 21/29* (2013.01); *G01N 21/84* (2013.01); *G01N 2021/8466* (2013.01)

(56) References Cited

U.S. PATENT DOCUMENTS

| | | | |
|---|---|---|---|
| 5,278,423 A | 1/1994 | Wangler et al. | |
| 5,296,702 A * | 3/1994 | Beck | A01M 7/0089 |
| | | | 250/226 |
| 5,439,490 A | 8/1995 | Janus | |
| 5,606,821 A | 3/1997 | Sadjadi et al. | |
| 5,911,669 A | 6/1999 | Stentz et al. | |
| 6,178,253 B1 | 1/2001 | Hendrickson et al. | |
| 6,269,617 B1 | 8/2001 | Blanchard | |
| 6,374,584 B1 | 4/2002 | Blanchard | |
| 6,443,365 B1 * | 9/2002 | Tucker | A01M 7/0089 |
| | | | 239/155 |
| 6,556,598 B1 | 4/2003 | Angott | |
| 6,573,512 B1 * | 6/2003 | Lucia | G01N 21/6402 |
| | | | 250/458.1 |
| 6,795,568 B1 | 9/2004 | Christensen et al. | |
| 7,081,611 B2 | 7/2006 | Scott | |
| 7,619,801 B1 | 11/2009 | Shih et al. | |
| 7,916,898 B2 * | 3/2011 | Anderson | A01B 69/008 |
| | | | 250/334 |
| 8,027,770 B2 | 9/2011 | Poulsen | |
| 8,179,533 B2 | 5/2012 | Alameh | |
| 8,340,402 B2 | 12/2012 | Schmitt et al. | |
| 8,792,531 B2 * | 7/2014 | McCallion | G02B 26/0883 |
| | | | 359/298 |
| 2006/0132613 A1 | 6/2006 | Shin et al. | |
| 2008/0095402 A1 | 4/2008 | Kochi et al. | |
| 2008/0244970 A1 | 10/2008 | Ide et al. | |
| 2010/0186284 A1 | 7/2010 | Hyde et al. | |
| 2010/0268391 A1 | 10/2010 | Anderson | |
| 2011/0166705 A1 | 7/2011 | Anderson et al. | |
| 2011/0211733 A1 | 9/2011 | Schwarz | |
| 2013/0182077 A1 | 7/2013 | Holz et al. | |
| 2013/0182079 A1 | 7/2013 | Holz et al. | |
| 2013/0182897 A1 | 7/2013 | Holz et al. | |
| 2013/0182902 A1 | 7/2013 | Holz et al. | |

FOREIGN PATENT DOCUMENTS

| | | |
|---|---|---|
| DE | 102004011462 | 9/2005 |
| DE | 102007036222 | 2/2009 |
| WO | WO9402812 | 2/1994 |
| WO | WO9717830 | 5/1997 |
| WO | WO00/03589 | 1/2000 |
| WO | WO0217705 | 3/2002 |
| WO | WO02091823 | 11/2002 |
| WO | WO2006021207 | 3/2006 |
| WO | WO2007054998 | 5/2007 |
| WO | WO2008014553 | 2/2008 |
| WO | WO2008124333 | 10/2008 |
| WO | WO2010083053 | 7/2010 |
| WO | WO2012175809 | 12/2012 |

OTHER PUBLICATIONS

Jul. 1, 2015, File History for U.S. Appl. No. 14/027,116.
2005, Moller et al., "Robust 3D Measurement with PMD Sensors", Proceedings of the 1st Range Imaging Research Day at ETH, 2005, 14 pages.
Jul. 20, 2009, Rubenchik et al., "Environmentally Clean Mitigation of Undesirable Plant Life Using Lasers", Lawrence Livermore National Laboratory, Jul. 20, 2009, 7 pages.
2011, Piron et al., "Weed Detection in 3D Images", Precision Agric., vol. 12, 2011, pp. 607-622.
2013, Sun et al., "3D Computational Imaging with Single Pixel Detectors", Science, vol. 340, 2013, 5 pages.
Aug. 5, 2016, File History for EP App. No. 14183824-3 as retrieved from the EP Electronic File System on Aug. 5, 2016, 82 pages.
Jul. 25, 2016, File History for U.S. Appl. No. 14/027,120.
Aug. 5, 2016, File History for EP App. No. 14183822.7 as retrieved from the EP Electronic File System on Aug. 5, 2016, 75 pages.

* cited by examiner

UNWANTED PLANT REMOVAL SYSTEM HAVING VARIABLE OPTICS

TECHNICAL FIELD

Embodied is a system for removing unwanted or undesirable plants that includes an imager, image processor, laser device, and guidance system.

BACKGROUND

Removal of undesirable plants or weeds is a problem that has been plaguing agriculture and horticulture for a long period of time. Typically, unwanted plants or vegetation can be removed physically, for example, by a hoe or cultivator; chemically, for example, by the use of herbicides; or biologically, for example, by a bio-agent such as an introduced insect or fungus that can target the unwanted vegetation. Physical removal of unwanted plants or vegetation can require human intervention which can be expensive or time-consuming. Chemical removal of unwanted plants or vegetation can require the use of chemical agents that can contaminate drinking water, have long term environmental consequences, and can be otherwise unfriendly to the environment. Biological removal of unwanted plants and vegetation can be hard to control and is not always effective and efficacious.

SUMMARY

In one aspect, embodiments include a three-dimensional imager configured to capture plant images and locate plants, an image processor configured to distinguish between a wanted plant and an unwanted plant based on the captured plant images, a laser device configured to emit a laser beam having power sufficient to damage a target on the unwanted plant, and a guidance system configured to direct the laser beam towards the target of the unwanted plant. The laser device can have a variable depth of field, a variable width of field, a variable focal length, or a combination thereof. The embodied apparatus also includes a chassis configured to support the three-dimensional imager the at least one laser device, and, optionally, the guidance system. The chassis is configured to be moved across an area.

In another aspect embodiments of a lawn weeding system include a lawn mower that includes a cutting means and an unwanted plant removal apparatus. The cutting means can include a mechanical blade, a flame, or can be electro-optical and include, for example, a laser cutting system. In some embodiments, the lawn mower can generate power to energize at least one of the three-dimensional imager, the image processor, the at least one laser device, and the guidance system.

In yet another aspect, embodiments include a method of removing unwanted plants that include capturing plant images using a three-dimensional imager, distinguishing between a wanted plant and an unwanted plant after capturing plant images, and locating a target on the unwanted plant. The method also includes guiding at least one laser device configured to emit a laser beam to the target of the unwanted plant, adjusting a depth of field, a width of field, or a focal length of the laser beam; directing the adjusted laser beam to the target of the unwanted plant; and damaging the target of unwanted plant with the laser beam. The embodied methods also can include moving the chassis across a designated area.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings, where like reference numerals designate like elements, and wherein.

In the present disclosure:

"diode bars" refer to high-power semiconductor lasers (laser diodes) containing a one-dimensional array of broad-area emitter, or alternatively subarrays containing 10-50 narrow stripes;

"FAST" axis refers to the emission from a laser diode (having output with an elliptical cross section) along the elliptical axis that has the largest divergence angle and lowest effective refractive index—the other elliptical axis is referred to as the normal or "SLOW" axis;

"accelerometers", "galvo mirrors", or "galvo scanners" refer to devices that are responsive to electronic signals—the accelerometer can sense force (gravity, for example) and convert the force to an electronic signal; the mirror can change reflection angles based upon an electronic signal; and the scanner can direct a sweep of a laser beam over a large angle;

"microaccelerators", "micromirrors", or "microscanners" are MEMS integrated sensor or actuator devices used interchangeably with "galvo accelerometers", "galvo mirrors", or "galvo scanners" and typically have a much smaller form factor and higher level of integration; and "Rayleigh range" refers to the distance along the propagation direction of a beam from its waist or narrowest beam cross section to the place where the cross-sectional area is doubled.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Figure 1:
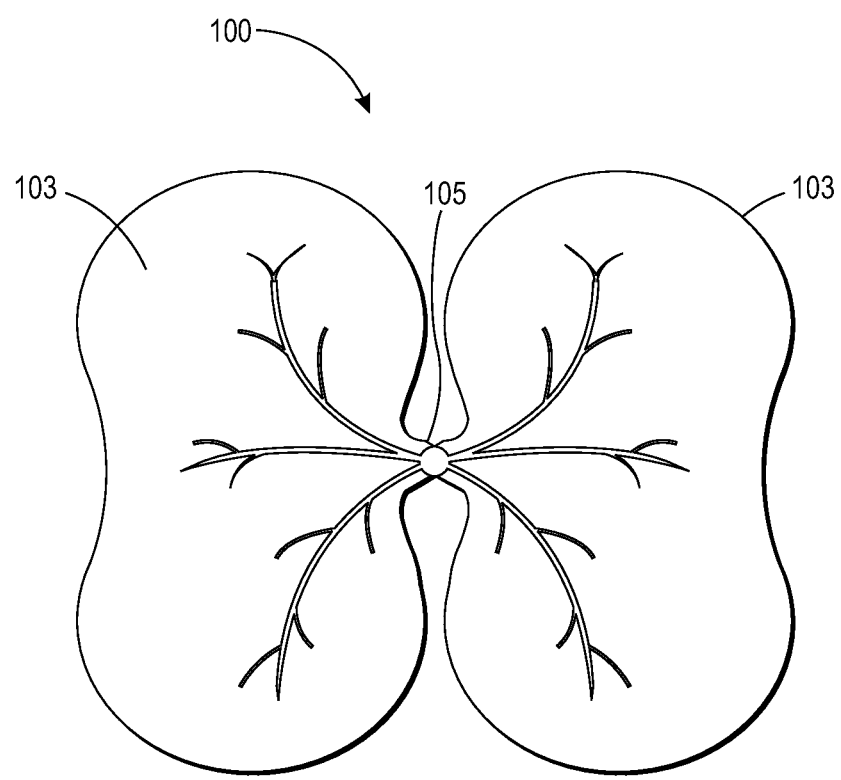
FIG. 1 is a schematic drawing showing parts of an emerging seedling.
Figure 2:
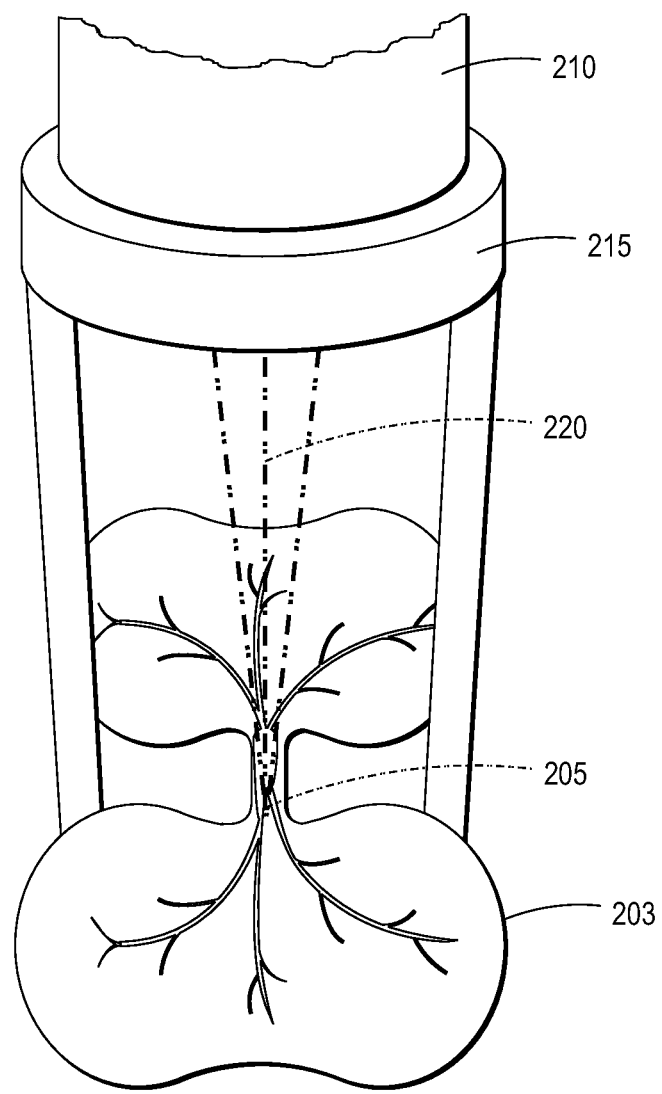
FIG. 2 is a schematic drawing of a laser focused on the meristem of an emerging seedling.

Typically, when a seedling of a plant germinates two initial leaves emerge from the ground. These leaves, called cotyledons, provide energy in the form of stored energy and the beginnings of photosynthesis to allow the seedling to begin growth. FIG. 1 is a schematic drawing showing parts of emerging seedling 100. Seedling 100 has two cotyledons 103 that are attached to each other and to the emerging stem by meristem 105. FIG. 2 is a schematic drawing of a laser focused on the meristem of an emerging seedling. FIG. 2 shows laser 210 mounted on stand 215 having laser beam 220 focused on meristem region 205 of unwanted plant 203.

The most effective position to target for laser destruction of a weed or unwanted plant is the small meristem region. The meristem region contains stem cells that can promote further growth of the weed or unwanted plant. Typical unwanted plants or weeds have a target meristem region on the order of 1 mm or less available for laser destruction in order to stop growth. As an unwanted plant grows larger it takes more energy for an effective kill. Killing an unwanted plant just after it emerges can eliminate strong root formation and doom the plant's growth. $CO_2$ laser emissions have high optical absorption in the carbon hydrovibrational bands of plant matter. In the early stage of growth a $CO_2$ laser (wavelength of 10.6 μm) can kill an emerging seedling with an effective dose of 0.1 J/mm. However, due to the long wavelength, there is a limit to the smallest spot size that can be achieved in a wide field of view system. Thus, to make a practical laser system for destroying unwanted plants using a $CO_2$ laser, high power (along with an accompanying power supply) is needed to produce enough exposure in a 1 mm spot to kill the plants. Thus, the wavelength of the $CO_2$ laser has limited the usefulness of this laser for damaging unwanted plants in a commercial apparatus.

Figure 3:
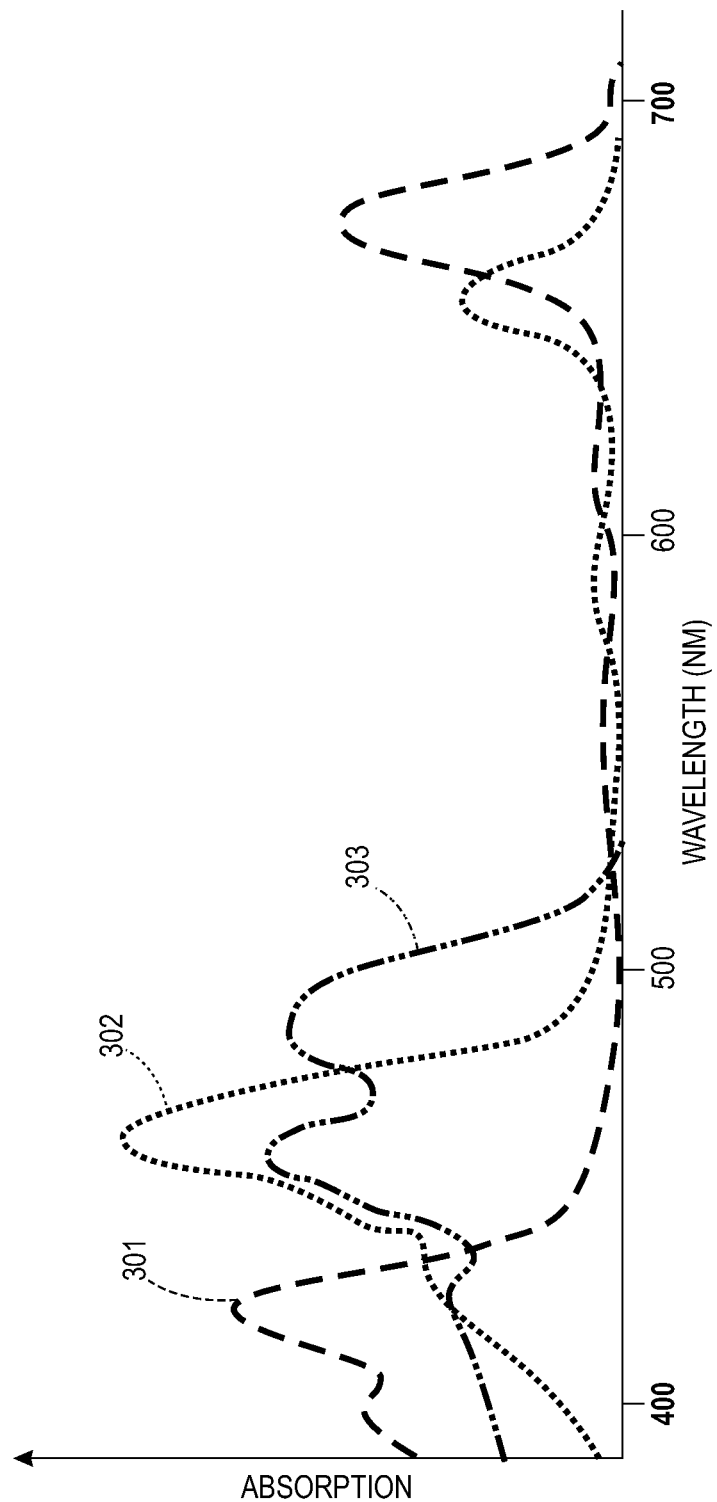
FIG. 3 is a graph of absorption vs. wavelength (nm) of chlorophyll A, chlorophyll B, and carotenoids.

FIG. 3 is a graph of absorptions vs. wavelength (nm) of plant pigments, chlorophyll A 301, chlorophyll B 302, and carotenoids 303 that are typically present in plants. As can be seen in FIG. 3 the optimum wavelengths for energy absorption in the visible wavelength range for plant pigments can be in the 430 nm-475 nm range or in the 650 nm-675 nm range. High power red and blue diode bars and single mode semiconductor sources have been commercialized that can have powers over 1 Watt in each of these wavelength ranges. For example, semiconductor laser diodes or diode bars that can reach powers of greater than about 300 mW or up to about 5 Watts (or greater) in the blue range (430 nm-475 nm) and up to about 20 Watts (or greater) in the red range (650 nm-675 nm) are suitable for applications disclosed herein.

Devices and methods disclosed herein use a three-dimensional imager to locate and identify unwanted plans, a laser device useful to damage and kill unwanted plants, and a guidance system to direct a beam from the laser device towards the unwanted plant. The three-dimensional imager, laser device, and guidance system can be supported by a chassis that can be configured to be moved across an area such as an agricultural field or a lawn. Unwanted plant removal systems that include advanced imaging systems are disclosed in co-filed and co-owned U.S. patent application Ser. No. 14/027,116, filed the same day herewith. Unwanted plant removal systems that include stabilization systems are disclosed in co-filed and co-owned U.S. patent application Ser. No. 14/027,120, filed the same day herewith. These two applications are herein incorporated by reference in their entirety.

An apparatus in accordance with some embodiment, includes a three-dimensional imager configured to capture plant images and locate plants, an image processor configured to distinguish between a wanted plant and an unwanted plant based on the captured plant images, a laser device configured to emit a laser beam having power sufficient to damage the unwanted plant, and a guidance system configured to direct the laser beam towards the unwanted plant. The laser device has at least one of a variable depth of field, a variable width of field, a variable focal length, or a combination thereof. Embodiments of the apparatus also include a chassis configured to support the three-dimensional imager and the laser subsystem. The chassis is also configured to be moved across an area.

In some embodiments, an apparatus utilizes a three-dimensional imager that can be configured to work at focal lengths between about 10 cm and 1 m and that allow the apparatus to capture plant images and locate plants that have characteristics of unwanted plants. In some cases, the imager, e.g., three-dimensional imager, can take advantage of color information for plant identification. Additionally, in some embodiments, a three-dimensional imager and guidance system can capture the three-dimensional position of the meristem of unwanted plants and use this data to direct the laser beam so as to better target laser absorption by the meristem of the unwanted plant. In some embodiments, the three-dimensional imager can include stabilization lenses for low light stabilization.

In some embodiments, a three-dimensional imager can provide positioning (location) of objects such as unwanted plants and the location of targets on unwanted plants by the use of geometric systems (triangulation) or electronic systems (utilizing time-of-flight (TOF) measurements). In some embodiments, a triangulation-based imager can include a three-dimensional stereo camera system that includes two camera separated by a known distance or baseline. In some embodiments, the triangulation-based imager can include a single or multiple beam laser scanner and a single camera separated by a known distance or baseline. In some embodiments, the triangulation-based imager can include a single or multiple beam laser scanner and a stereo camera wherein the stereo camera includes two cameras separated by a known distance or baseline. In some embodiments, the triangulation-based imager can include a structured light illuminator and a camera separated by a known distance or baseline. Some embodiments involve a digital light projector (DLP) configured to project light that may be used in conjunction with three-dimensional imaging. In all of these embodiments, the depth (z-direction) accuracy of the three-dimensional imager increases as the baseline distance increases.

Figure 4:
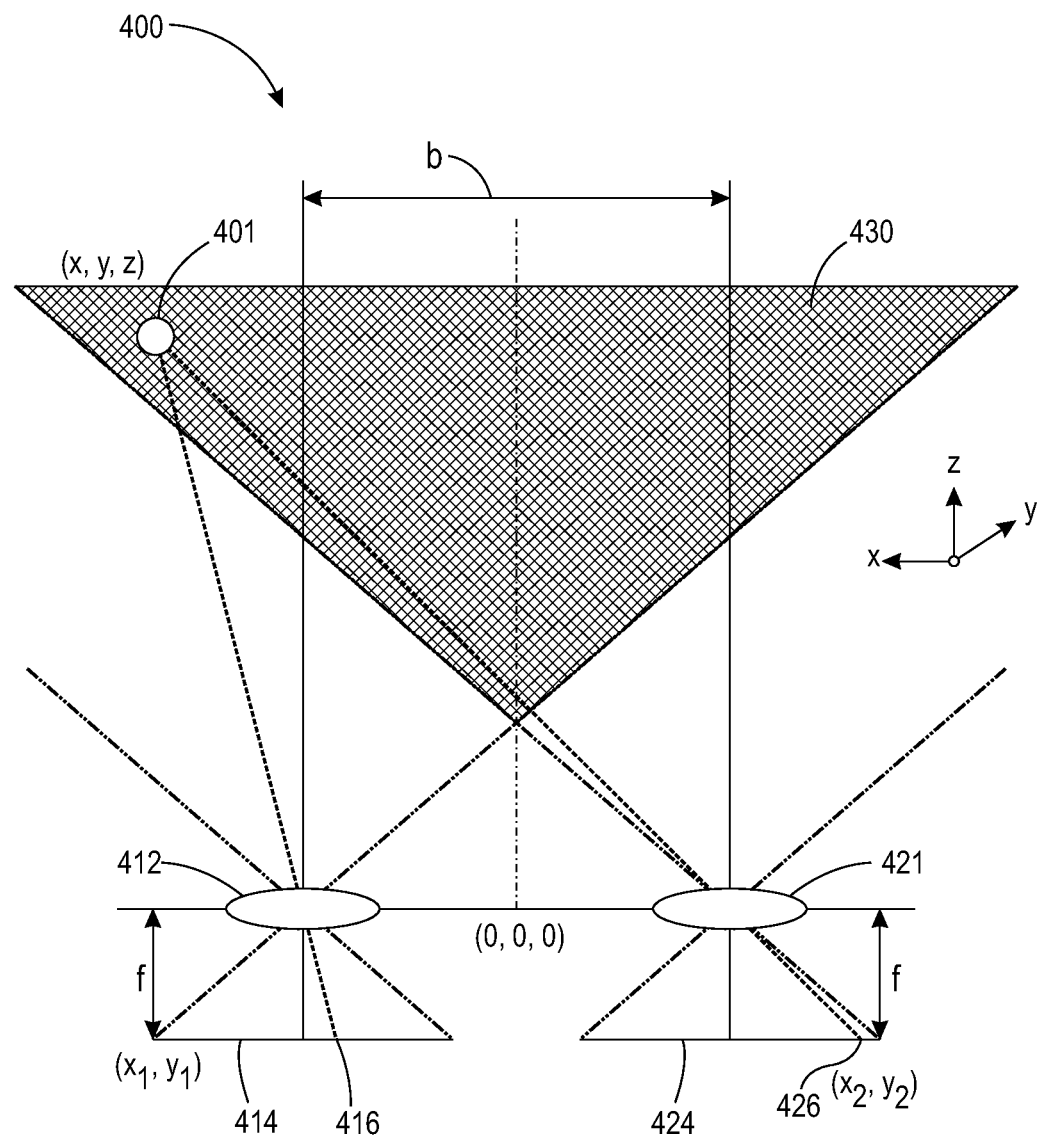
FIG. 4 is a schematic drawing of a stereoscopic three-dimensional imaging system useful in an embodiment of an apparatus that includes two cameras.

FIG. 4 is a schematic drawing of a stereoscopic three-dimensional imaging system useful in an embodiment of the disclosed apparatus that includes two cameras separated by a known distance or baseline. A planar section of stereoscopic three-dimensional imaging system 400 is shown in FIG. 4 along the x, z plane with two stereo cameras spaced apart along the x direction at a distance of b. The first camera is illustrated by camera aperture 412 having a lens with a focal length "f" distant from two-dimensional sensor array 414 which is in the x, y plane. Two-dimensional sensor array 414 can be, for example, a charge-coupled device array (CCD) which lies in the x, y plane. Similarly, the second camera is illustrated by camera aperture 422 having a lens with a focal length "f" away from two-dimensional sensor array 424 which is in the x, y plane. Point or volumetric picture element (voxel) 401 with coordinates (x, y, z) is located in space within conical three-dimensional field of view 430, an x, z planar slice of which is shown in FIG. 4. Point or voxel 401 is mapped to locations 416 on two-dimensional sensor array 414 and 426 on two-dimensional sensor array 424. From this information, the three-dimensional location (x, y, z) can be determined by the following equations:

$$x = b(x_1 + x_2)/2 \cdot (x_1 - x_2)$$

$$y = b(y_1 + y_2)/2 \cdot (x_1 - x_2)$$

$$z = b \cdot f/(x_1 - x_2)$$

Figure 5:
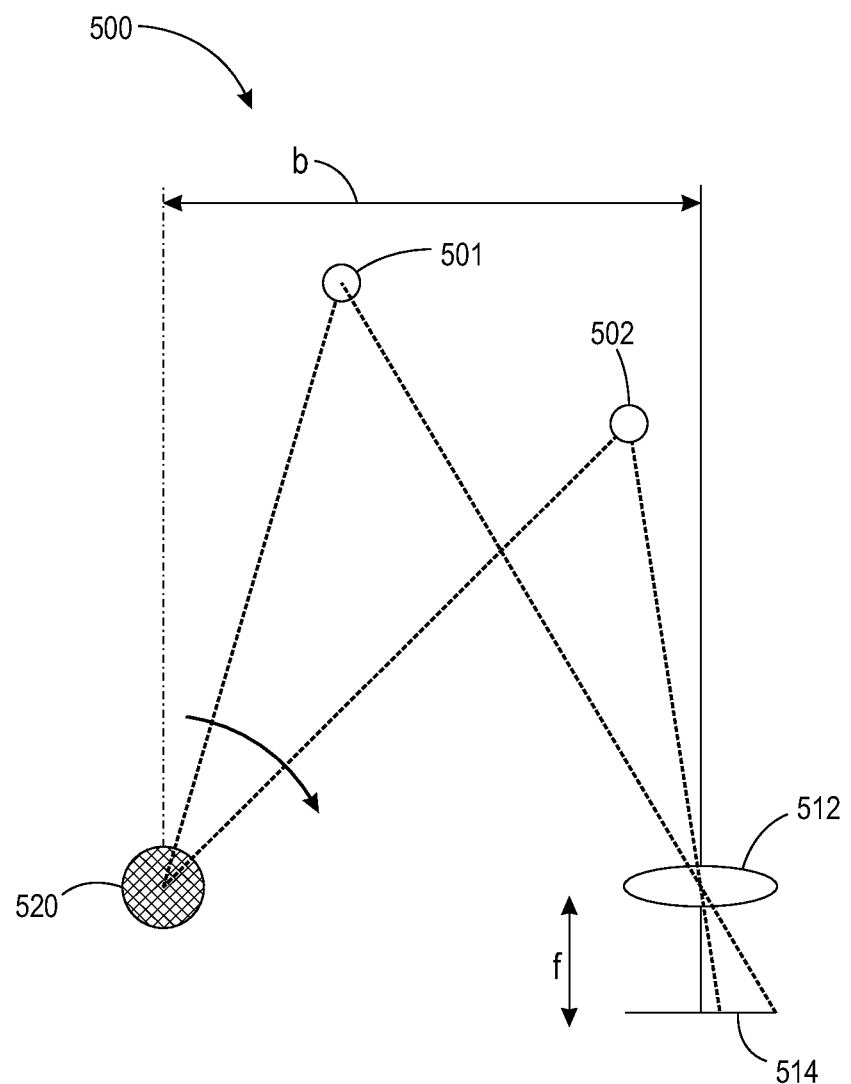
FIG. 5 is a schematic drawing of a three-dimensional imaging system useful in an embodiment of an apparatus that includes a multiple beam laser scanner and one camera.

FIG. 5 is a schematic drawing of a three-dimensional imaging system useful in an embodiment of the apparatus that includes a multiple beam laser scanner and one camera. Three-dimensional imaging system 500 includes laser scanner 520 and one camera illustrated by camera aperture 512 having a lens with a focal length "f" distant from two-dimensional sensor array 514 which is in the x, y plane. Laser scanner 520 can illuminate a three-dimensional location of two voxels 501 and 502. In the illustration shown in FIG. 5, laser scanner 530 maps each voxel 501 and 502 to two different locations on two-dimensional sensor array 514 depending on the angle of incidence between the laser scanner and the voxel. From this information the position and dimensions of the voxel can be determined.

Figure 6:
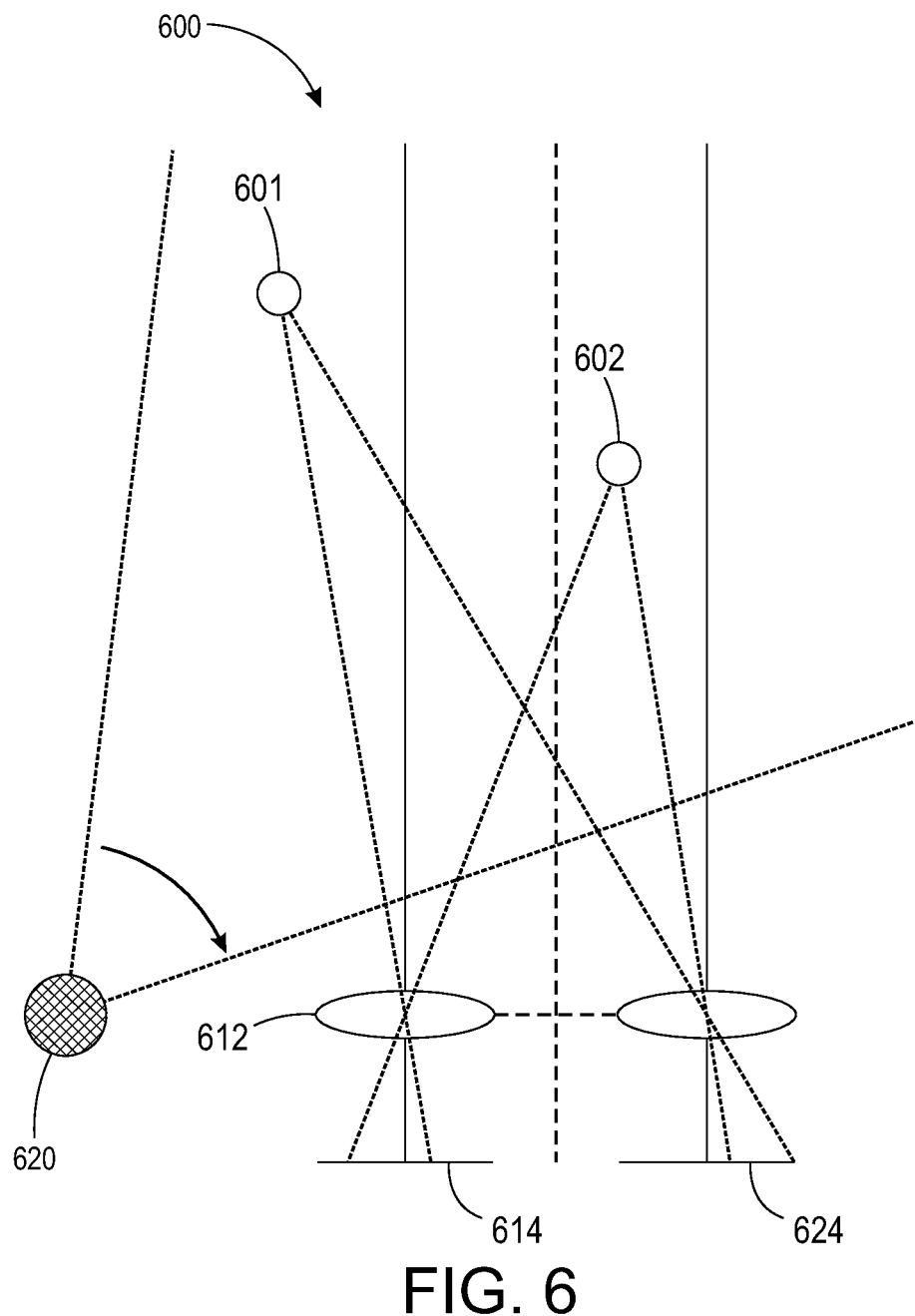
FIG. 6 is a schematic drawing of a stereoscopic three-dimensional imaging system useful in an embodiment of an apparatus that includes a laser scanner and a stereo camera.

FIG. 6 is a schematic drawing of a stereoscopic three-dimensional imaging system useful in an embodiment of the apparatus that includes a laser scanner and a stereo camera. Three-dimensional imaging system 600 includes laser scanner 620 that can scan a range of solid angles as shown in the illustration. Points or voxels 601 and 602 are, thus, optically mapped by two cameras, the first one depicted by aperture 612 and two-dimensional sensor array 614 and the second one depicted by aperture 621 and two-dimensional sensor array 624. The relative positions of the image of voxel 601 on two-dimensional sensor arrays 614 and 624 illuminated by laser scanner 620 can be used to determine three-dimensional coordinates of that voxel. Similarly the relative positions of the image voxel 602 on two-dimensional sensor arrays 614 and 624 illuminated by laser scanner 620 can be used to determine three-dimensional coordinates of that voxel. If voxel 601 and 602 are different points on the same object such as, for example, the base and height of an unwanted plant, the location and height of that plant can be determined. In this way multiple points on a three-dimensional object can be mapped to give a mathematical location of that object in three-dimensional space.

Cameras in each of the illustrated embodiments can be placed in an array that can then be used to image an entire row of, for example, crops in an agricultural field using one pass of the imaging system. Laser scanning (raster scanning) can also be accomplished with a light source having one or more scanning beams in combination with collection optics and one or more detectors.

Electronic systems that employ time-of-flight (TOF) methodology can also be used for three-dimensional imaging. TOF three-dimensional imaging is based upon the indirect estimation of arrival time by measuring the phase shift between a transmitted and received signal. TOF three-dimensional imaging systems include a light source that can emit modulated or coded illumination and a detector or detector array (two-dimensional sensor array) that can measure the phase difference or the time difference between the emitted light and the light captured by the detector or detector array after being backscattered from an object in an image field. Typical TOF sensors employ incoherent, near-infrared, amplitude-modulated, continuous-wave light. The signal phase shift or time difference (and hence the object distance) can be used to generate a three-dimensional map or a three-dimensional point cloud of objects in the field of view. In some embodiments, lasers can be used to generate this information, using coherent, near-infrared, amplitude-modulated, pulsed light. The light used for TOF imaging can be discriminated from ambient or background light. For this reason, TOF imaging systems can be insensitive to variations in lighting conditions such as, for example, shading, obscurations, surface textures and colors, and unwanted specular reflections.

Figure 7:
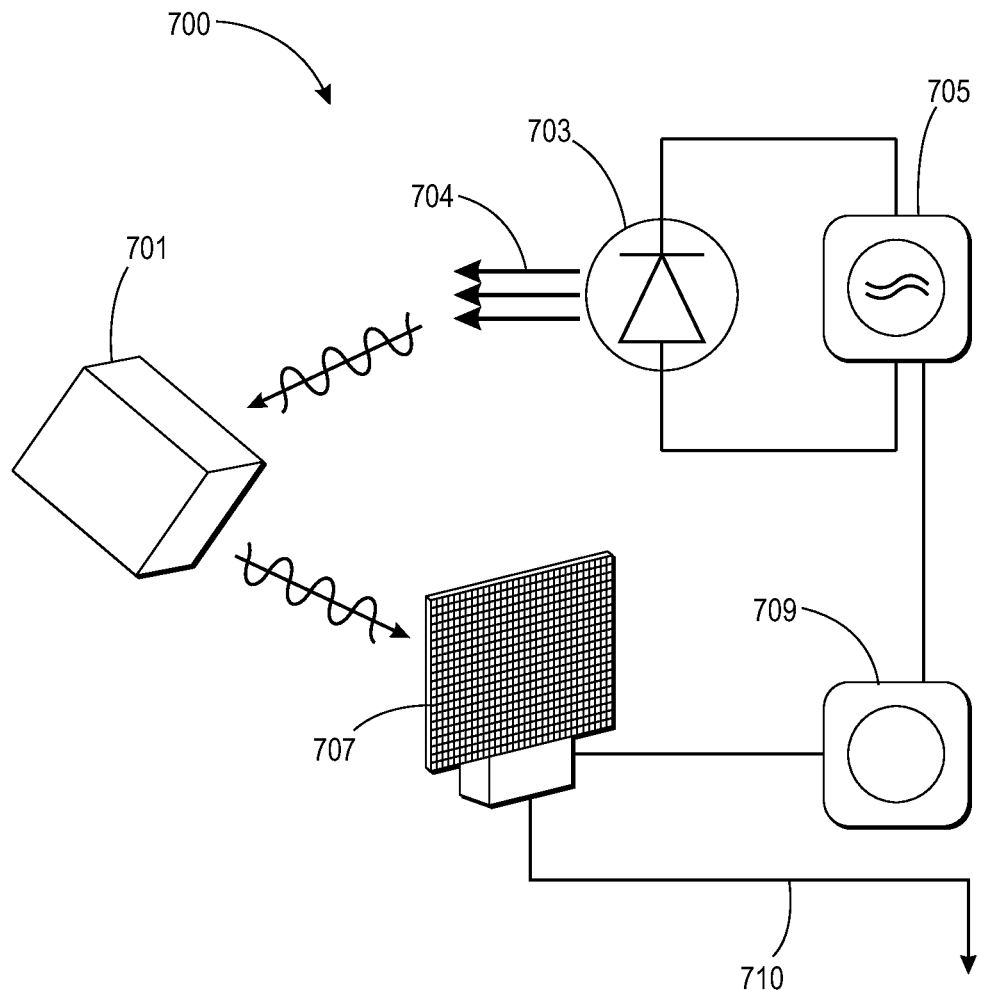
FIG. 7 is a schematic drawing of a time-of-flight three-dimensional imager useful in an embodiment of an apparatus.

FIG. 7 is a schematic drawing of a TOF three-dimensional imager useful in an embodiment of the apparatus. TOF three-dimensional imager 700 includes a photonic mixer device (PMD) based range imaging camera. PMD camera includes modulator 705 that modulates IR light source 703 so as to produce a modulated IR beam that can be transmitted to each voxel of three-dimensional object 701 as shown. Each voxel of three-dimensional object 701 can create a phase shift as the modulated IR beam is reflected off of its surfaces. The phase shifted IR beam is then captured by CCD array 707. The phase shift is measured by comparison to phase shifted signal 709 for each voxel and can produce data 710 that can then be used to produce a three-dimensional map of object 701. Recently TOF cameras have dramatically come down in cost as hands free gesture recognition systems are starting to become a popular for computer gaming. One such example is the Camboard pico 3D, with a TOF camera made by PMD technologies gmbH located Germany. Such a camera can subtract out background light and has improved near-field depth sensing accuracy with the ability to sense objects at distances as close as 15 cm.

Another time-of-flight three-dimensional measurement system is based upon light detection and ranging (LIDAR)

which is an optical remote sensing technology that can measure the distance to, or other properties of target objects by illuminating the object with laser light and then analyzing the backscattered light. Three-dimensional information about the shape and position of a three-dimensional object can be obtained from direct measurements of pulses from a scanning laser or the measurement of phase differences from a scanning laser.

Figure 8A:
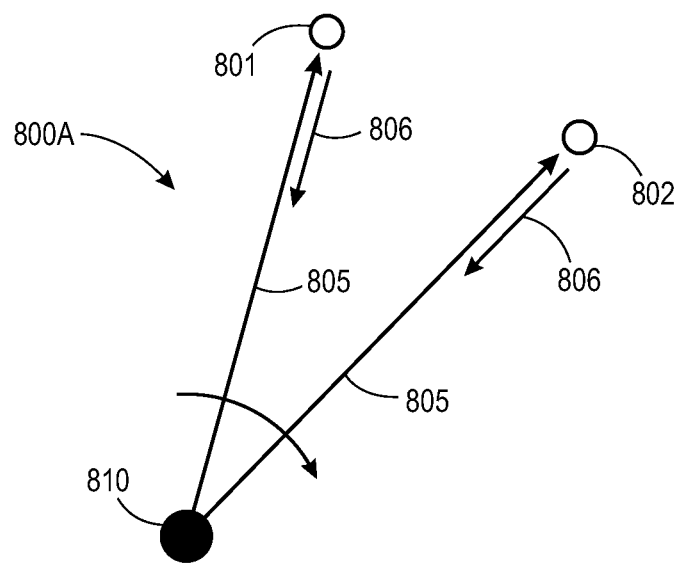
FIGS. 8A and 8B are schematic drawing illustrating light detection and ranging (LIDAR).
Figure 8B:
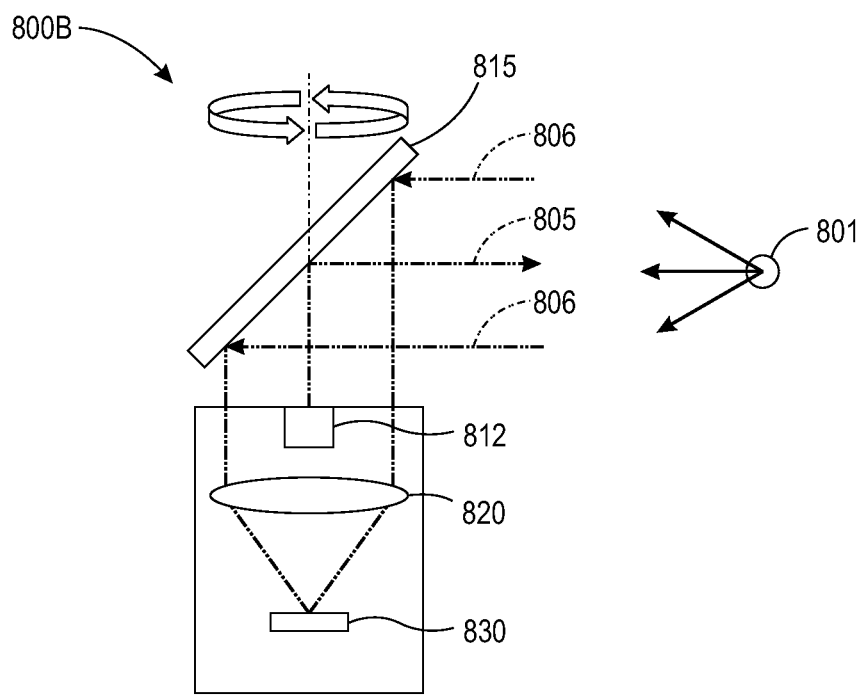

FIGS. 8A and 8B are schematic drawings illustrating an embodiment of LIDAR. FIG. 8A is a schematic drawing of LIDAR scanner 800A. LIDAR scanner 800A produces modulated scanning spots or scanning lines 805 from laser scanner 810 as it sweeps through space in a direction shown by the arrow in FIG. 8A. Some of the scanning spots or scanning lines 805 are reflected back as reflected return pulses 806 when they hit a pixel (pixel 801 or 801, for example) as shown by the reflection arrows.

FIG. 8B is an illustration of an embodiment of a detection system that can measure reflected return pulses that can be used to determine object shape and position by TOF. Detection system 800B includes a laser scanner (laser source 812 and scanning mirror 815) that emits scanning lines 805 over a scanned area. If light from a scanning line 805 hits a pixel (such as pixel 801 or 802), a reflected return pulse 806 can be reflected back to scanning mirror 815, through optional focusing element 820 onto detector 830. Signal processing can determine shape and position of pixel 801 or pixel 802 (which can be part, for example, of an object or a point in time of a moving object).

Figure 9A:
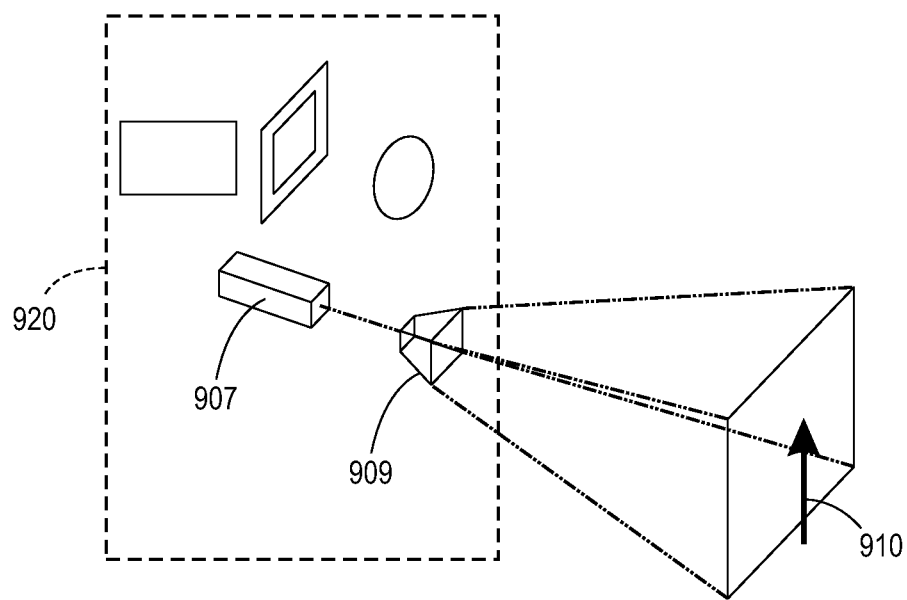
FIGS. 9A and 9B are schematic drawings of a time-of-flight three-dimensional imager useful in an embodiment of an apparatus.
Figure 9B:
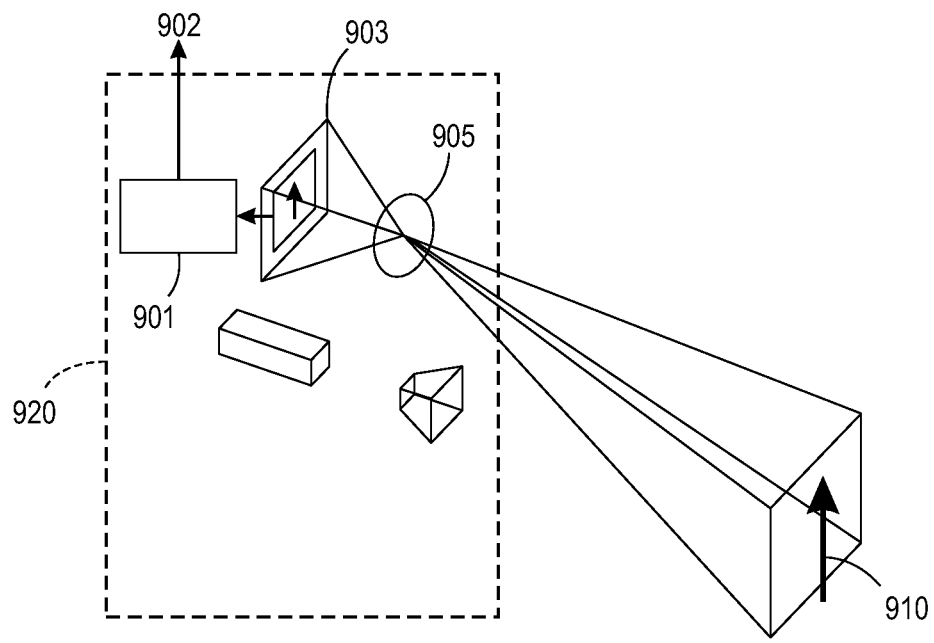

FIGS. 9A and 9B are schematic drawings of a TOF three-dimensional imager based upon LIDAR useful in an embodiment of the apparatus. FIG. 9A depicts the operation of TOF imager 900 in the transmit mode. FIG. 9B depicts the operation of TOF imager 900 when it received the backscattered light from a transmission. LIDAR components (shown in box 920) include laser 907 that can project light through beam spreader or collimator 909 to illuminate object 910 as shown in FIG. 9A. The backscattered light then goes through lensing component 905 that directs the light to an array of receivers 903 and then the data from the array is fed into digital image processor 901. A three-dimensional map or point cloud of objects can be generated from the data 902.

An additional approach to locating the three-dimensional position of unwanted plants as well as the meristem of emerging seedlings can be the use of a light-field or plenoptic camera. Plenoptic cameras contain light path information by putting low cost microlens arrays near the focus of a typical low cost CCD digital camera. Such cameras limit lateral resolution but have enhanced depth of field. Plenoptic cameras can generate a three-dimensional image by using computer processing in, for example, an image processor, to find the optimum focus for each position within a field of view. The resolution of plenoptic cameras is sufficient to image and precisely locate the meristem of an emerging unwanted seedling provided that the line of sight is not obstructed. The z-depth of focus can be improved and the height of the unwanted seedling and the location of its meristem can be estimated from computational imaging calculations in the image processor which can extract depths (in the z-direction) from information encoded in the plenoptic camera's microlens array.

Embodiments of the three-dimensional imager can collect full frame images during a short acquisition time or can utilize raster scanning. Full frame image collection requires the use of an imaging lens and a two-dimensional sensor array as discussed above. Raster scanning can be accomplished with a light source with one or more scanning beams in combination with collection optics and one or more detectors. Raster scanning requires more time than full frame image collection to cover the entire field of view.

In some embodiments, the apparatus includes an image processor configured to distinguish between a wanted plant and an unwanted plant based upon captured plant images from the three-dimensional imager. The image processor can take data (for example, plant images and plant locations) gathered by the three-dimensional imager and use that data to distinguish between an unwanted plant and a wanted plant. The image processor can also assist in the location of a target on the unwanted plant. The image processor can use digital comparison of collected digitalized plant image information with stored image information.

For weeds growing within a crop row, weed discrimination becomes more complex as leaf foliage from crop and weed may overlap and obstruct each other. Imaging algorithms are able to exploit RGB camera signals to discriminate foliage from ground soil and image processing algorithms are used to extract plant features, such as leaf shape and texture. In addition, multispectral imaging or hyperspectral imaging also allows different types of plants to be distinguished from their RGB and near-infrared (NIR) camera channel signals by comparing ratios of these various spectral channels. Both hyperspectral imaging and multispectral imaging collect and process information from across the electromagnetic spectrum. Based upon the size and species of weeds and crop, various combinations of image feature algorithms and multispectral or hyperspectral algorithms for imagers, e.g., three-dimensional imaging, may be employed.

Weed species typically have different growth characteristics from that of the mainline crop. These differences including differences in growth rates and seasonal variations when the seedlings develop through the top soil layer. Thus, three-dimensional imaging using stereoscopic and structured light approaches to measure plant height characteristics above the soil ground level can be used to identify weeds from crops independent of leaf shape and other plant morphology characteristics.

In some embodiments, weeds can be identified using a combination of imaging morphology as well as multispectral resolution. Multispectral imaging provides additional information as different plants seem to have different ratios of visible and near infrared absorption. Also, plant heights as measured by a three-dimensional camera give good distinction as weeds tend to grow at a different rate. The location of the weeds can also be used for their identification.

Some embodiments of the apparatus include a removal device for removing or damaging an unwanted plant. The removal device can include an herbicide applicator, a torch head for flame weeding, or a laser device. In one embodiment, the removal device can include a laser device configured to emit a laser beam having power sufficient to damage the unwanted plant. The amount of power sufficient to fatally damage an unwanted plant is dependent upon the wavelength of impinging radiation, the dose of that radiation delivered to the unwanted plant, the stage of development of the unwanted plant, and the part of the unwanted plant (target or area near the target) that is exposed to the impinging radiation.

In some embodiments, the at least one laser device can include a laser diode capable of emitting light that can be absorbed by plant pigments, such as chlorophyll A, chlorophyll B, and/or carotenoids. Typically, blue-emitting or red-emitting semiconductor laser diodes can be used since they can be configured to emit a laser beam having a wavelength of from about 430 nm to about 475 nm or from about 650 nm to about 675 nm. In some embodiments, the removal device can have an adjustable wavelength based upon information from the image processor. Laser devices can include individual laser diodes in an array such as in a laser diode bar.

Laser diode bars can be combined with FAST axis lenses and commercially available beam combiners to produce sources that have, in some instances, produced emissions as high as 20 Watts using 19 individual multimode laser emitters. In the FAST axis direction, single mode beam quality can be achieved. In the lateral SLOW axis direction, diffraction quality may not be achieved. When combining laser beams from multiple laser diodes, a lenslet (multilens) array can be used to collimate each beam individually. Spot sizes of 1-2 mm×100 μm can result from such combined beams from laser diode arrays. This type of beam shape can be good for articulating a cut near the meristem of an unwanted plant as long as several different laser positions and angles can be selected. Using laser diode bars or arrays along with a plurality of camera systems, the best angles for laser impingement on a particular unwanted plant can be chosen from many different laser diodes available on the laser diode bar. With blue and red high power lasers or laser diodes, the Rayleigh range for collimated light can be several meters along the FAST axis, which has high beam quality. With beam diameters of only 1 mm, microelectricalmechanical systems (MEMS) approaches to single axis large angle galvo scanners are suitable for implementations disclosed herein.

Embodiments of the apparatus include a guidance system configured to direct a laser beam towards the target of the unwanted plant. The guidance system can take information from the image processor and use beam direction changing devices such as, for example, galvo mirrors, to redirect and, in some embodiments, focus the laser beam on the target of the unwanted plant. In some embodiments, the laser beam can be directed to a particular part of the plant such as, for example, the meristem of the plant. In one embodiment, the guidance system can include a high power laser actuator array such as one illustrated in FIG. 9. In some embodiments, the laser beam controller can include a two-axis MEMS galvo mirror.

Figure 10:
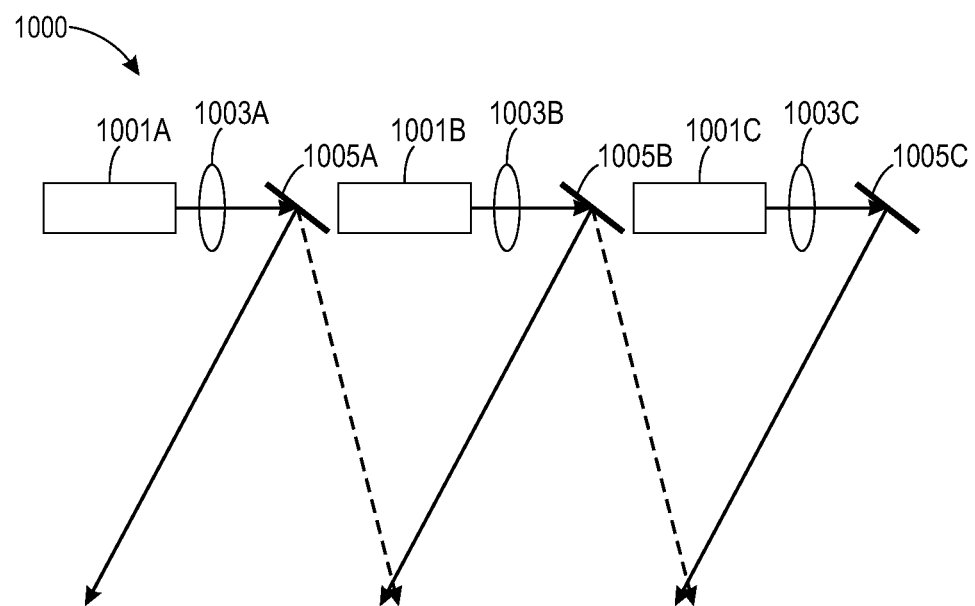
FIG. 10 is a schematic drawing of an array of laser diodes useful in an embodiment of an apparatus.

FIG. 10 is a schematic drawing of an array of laser diodes useful in an embodiment of a laser guidance system for the disclosed apparatus. Array 1000 is a laser device that includes an array of laser diodes 1001A-1001C that can be part of a laser diode bar. Although array 1000 as illustrated includes three laser diodes this is for illustrative purposes only and typical laser diode bars or arrays can have many more laser diodes than illustrated. Array 1000 includes a collection of collimation optics 1003A-1003C. A series of MEMS electrostatic mirrors 1005A-1005C take information from the image processor and direct one or more beams to a target unwanted plant. By changing the position of mirrors 1005A-1005C it is possible to direct multiple beams at each unwanted plant and/or to direct at least one beam to more than one unwanted plant as shown in FIG. 10. In some embodiments, the guidance system includes one or more adaptive optical elements such as a MEMS adaptive optical mirror that can be used to enhance the range of depth of focus of the laser beams. The mirrors can have reflective coatings compatible with the lasers used, e.g., blue or red semiconductor lasers. For example, the laser may be activated after is it directed to a specific target location, at a specified angle of impingement and/or at a specified depth of focus.

Figure 11:
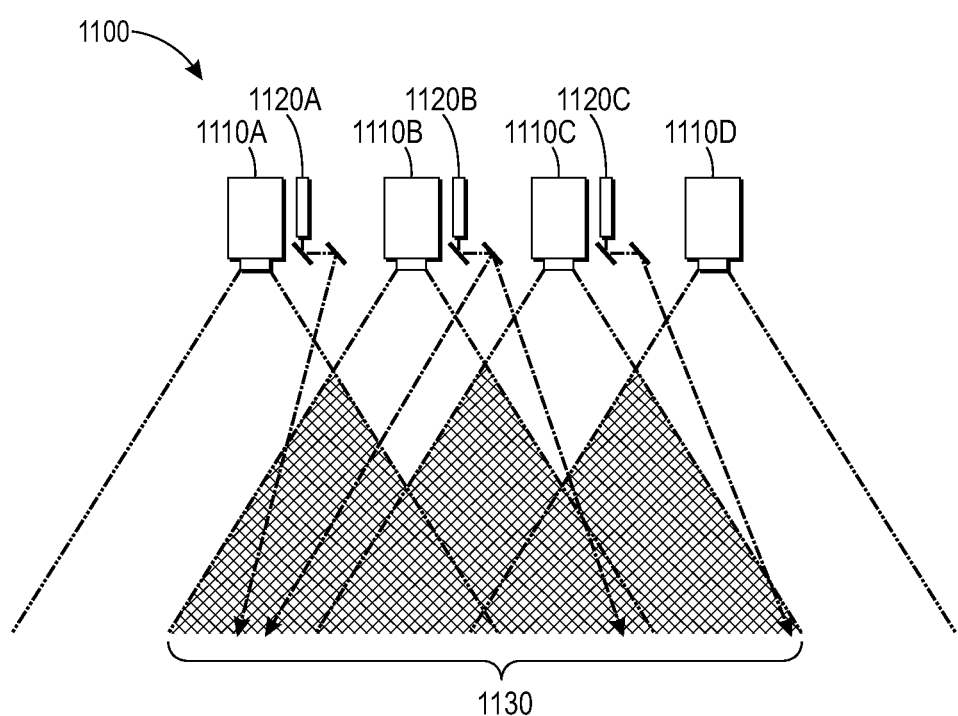
FIG. 11 is a side view of an array of laser diodes combined with a three-dimensional camera array that is useful in an embodiment of an apparatus.

In some embodiments, a laser diode array can be combined with an array of three-dimensional imagers (cameras) to allow for accurate pointing and optimal angular position of laser beams. In some configurations, the laser array and three-dimensional imagers can be adapted to provide width scalable, single pass weeding. One embodiment of a laser array and imager is illustrated in FIG. 11. Array 1100 includes array of three-dimensional cameras 1110A-1110D and array of laser diodes 1120A-1120C. Cameras 1110A-1110D cover an overlapping stereoscopic field of view as illustrated. They can be used to direct an array of laser diodes (such as that depicted in FIG. 10) across field of view 1130 to locate and direct laser beams to targets on unwanted plants in an array of wanted and unwanted plants.

Some embodiments of the apparatus include a guidance system configured to direct at least one laser beam towards a target on the unwanted plant. Additionally, the guidance system can be configured to adapt the optics of the at least one laser device to provide for accurate and efficient use of the components of the embodied apparatus to remove unwanted plants. In some embodiments, the guidance system can provide feedback to the three-dimensional imaging system so as to change at least one of the depth of field, the width of field, or the focal length. Each of the lasers 1120A-1120C can be directed and/or controlled independently of each other with regard to position, angle, spot size, and/or focal length, etc. In some implementations, the power, wavelength, and/or beam type (continuous wave (CW) or pulsed) of each laser can be independently controlled based on the targeted plant type. In some embodiments, the spot size of the laser beam can be less than about 100 μm and the collimation diameter of the beam less than about 1 mm.

Large field of regard laser scanning (e.g., +/−30 degrees in both x and y directions) can be achieved together with variable length focus control by MEMS-based mirror scanners and/or adaptive optical elements. Some implementations include variable reprogramming of the focus position on the fly so as to target weeds of different heights on the fly.

To enhance stabilization during movement of the laser subsystem, the laser subsystem and/or components thereof may be designed so that they do not mechanically resonate at frequencies less than about 500 Hz. For example, the lowest order resonance mechanical frequency of the laser subsystem and/or components thereof may be greater than 500 Hz or even greater than 1 kHz.

Some embodiments of the apparatus also include a chassis configured to support the three-dimensional imager, the laser device, and the guidance system. The chassis can be configured to move across an area that includes wanted and unwanted plants, such as an agricultural plot or a lawn. The chassis can be any frame on which the three-dimensional imager, the at least one laser device, and the guidance system are mounted. In some embodiments, the three-dimensional imager, the at least one laser device, and the guidance system that are supported by the chassis can sense and, utilizing the guidance system, adjust adaptable optics of the at least one laser device in all three-dimensions including vertical. In some embodiments, the chassis can be part of a motorized tractor or motorized vehicle. In some embodiments, the chassis can be separate from the motorized tractor or vehicle and can be, for example, the frame of a trailer that can be attached to a motorized vehicle. In some embodiments, the chassis can be part of an aircraft that is designed to fly over the area that includes wanted and unwanted plants. In some embodiments, the image processor can also be mounted on the chassis. In other embodiments, the image processor can be located remotely and can communicate with the guidance system via wire or remotely via, for example, a Wi-Fi connection.

Some embodiments of the apparatus can scan wide swaths of an area such as an agricultural field or lawn and can use the guidance system to distinguish between a wanted plant and an unwanted plant, locate an unwanted plant, locate targets on the unwanted plant, select a laser beam emitted from at least one laser device, adjust the optical properties of the laser beam, direct the laser beam with adjusted properties to the target of the unwanted plant, and damage the target of the unwanted plant with the laser beam. If the laser device includes a plurality of laser diodes, the guidance system can select one or more laser diodes of the plurality of laser diodes so as to enhance the ability of the laser beam to hit the target on the unwanted plant with sufficient precision and energy to impart fatal damage to the plant.

The guidance system can have a high bandwidth that allows it to correct for environmental vibrations to which the apparatus may be subjected. In addition, the guidance system can have the capacity to scale over a wide area without compromising laser spot intensity. For example, the laser device may include many directly modulated semiconductor lasers that can be independently directed and focused on targets of unwanted plants at various different angles. The guidance system can control which lasers in a laser device with a plurality of lasers can be selected, focused, and energized to damage targets of a plurality of unwanted plants as the apparatus is moved across an area. The guidance system can adjust, based upon the position of the apparatus in the area, vibrations caused by steering the apparatus as it is moved across the area, unevenness of the area in the depth, or z-direction, and the three-dimensional location of the target of each unwanted plant as determined by the image processor.

Figure 12:
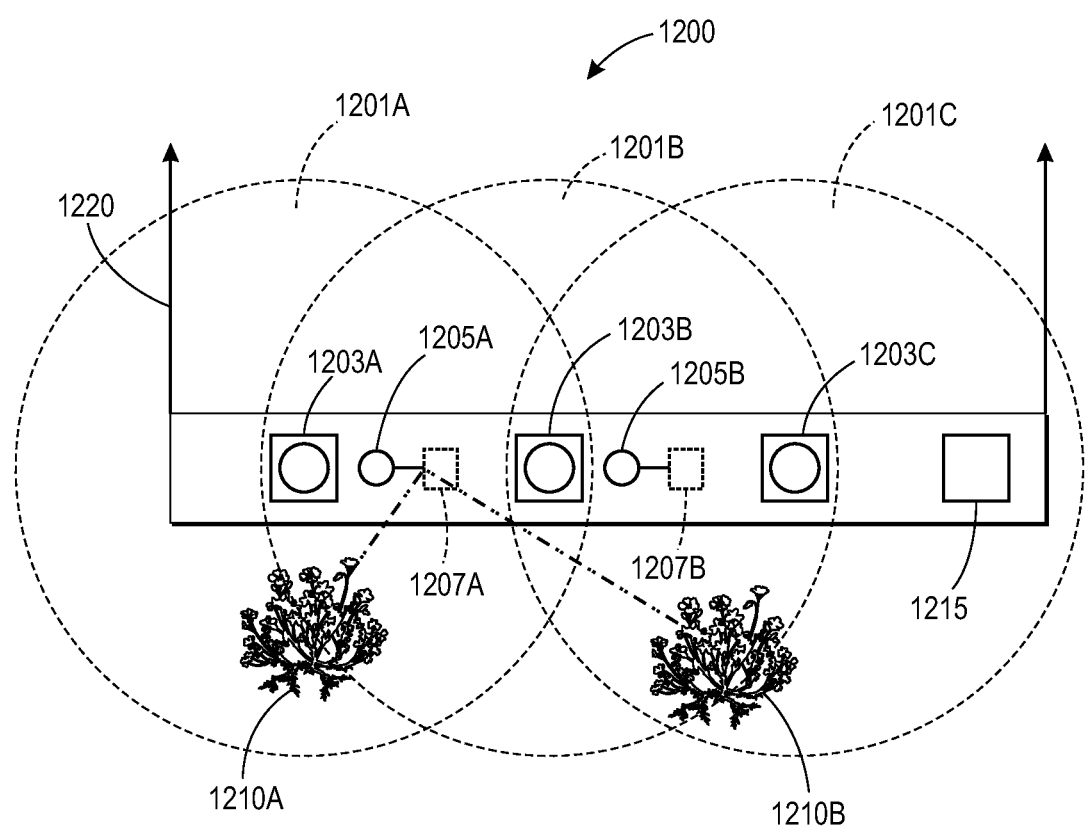
FIG. 12 is top view of an array of laser diodes and a three-dimensional camera array.

FIG. 12 is a schematic drawing of an embodiment of an apparatus that includes a guidance system that can adjust an array of semiconductor laser diodes. Apparatus 1200 includes a laser diode bar that, in the illustrated apparatus, includes three three-dimensional imagers 1203A, 1203B, and 1203C. Three-dimensional imager 1203A has field of view 1201A as shown (defined by depth of field, width of field, and focal length). Similarly, three-dimensional imagers 1203B and 1203C have respective fields of view 1201B, and 1201C. Fields of view 1201A, 1201B, and 1201C overlap as shown in FIG. 12. Three-dimensional imagers 1203 A-C are configured to distinguish between a wanted plant and an unwanted plant. Two unwanted plants, 1210A and 1210B, are shown for illustrative purposes. Apparatus 1200 is moved across a field that contains wanted and unwanted plants in the direction shown by arrow 1220. Apparatus 1200 also includes three-axis gyro accelerometer sensor 1215 that can sense mechanical vibrations such as those produced by an uneven field in the z-direction. In some embodiments, the three-axis accelerometer sensor can be configured to sense low frequency mechanical vibrations having a frequency of less than about 500 Hz. Apparatus 1200 has a guidance system that can take information from fields of view 1201A-C (via the image processor), and accelerometer sensor 1215. It can sense unwanted plants 1210A and 1210B and can direct changes in adaptive optics 1205A and 1205B that control the direction, depth of field, width of field, and focal length of laser beams emitted from laser diodes 1207A and 1207B respectively so that laser beams are directed at unwanted plants 1210A and 1210B as apparatus 1201 is moved across an area. In the embodiment illustrated in FIG. 12, two laser beams from laser diode 1207A are directed at both unwanted plant 1210A and 1210B although various combinations of lasers and adapted optics can be used to cover the whole area across which apparatus 1200 is traversed.

Figure 13:
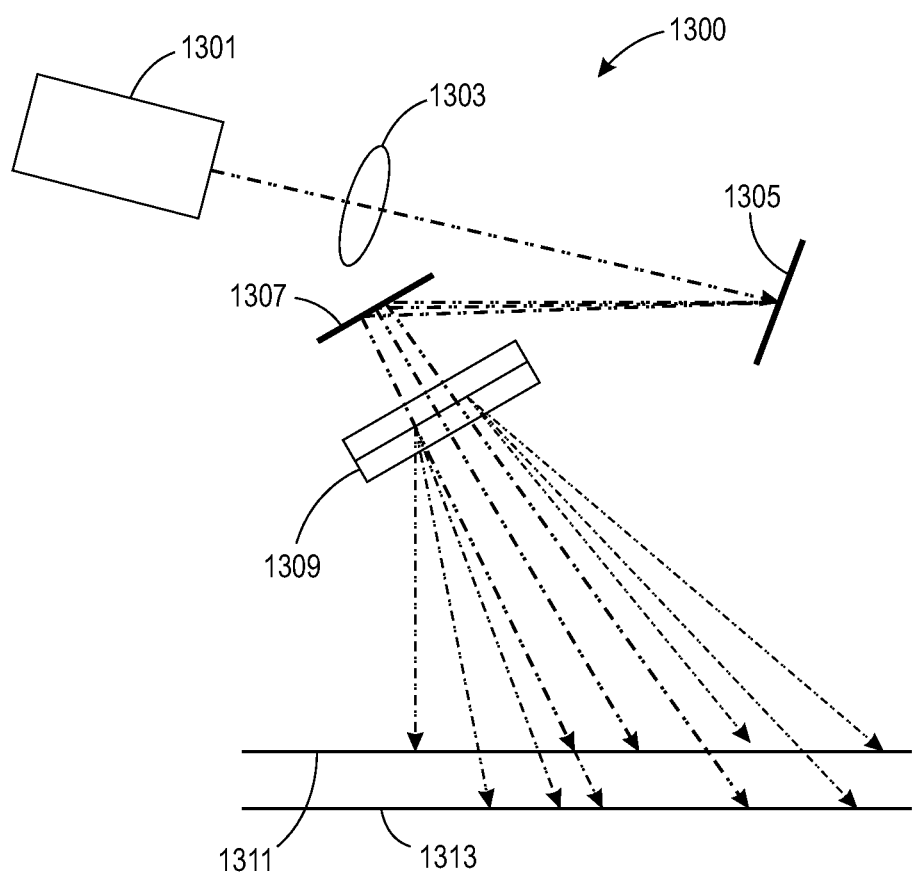
FIG. 13 is an illustration of non-mechanical phased array beam steering of a diode bar array.

FIG. 13 is an illustration of an embodiment of the apparatus that includes non-mechanical phased array beam steering of a diode bar array. Non-mechanical phased array steering module 1300 includes one or more arrays of single mode semiconductor lasers 1301 that are first collimated into one-dimensional optical phase modulators 1305 by collimating optics 1303. Each phase modulator 1305 has the power to change the direction and the focus point of the output light along one axis by reprogramming the phase of each individual phase modulation element. Additionally, the one-dimensional phase modulator has a large square aperture so that high power pulsed laser light has low enough intensity to not cause thermal heating issues inside the modulator. The phase modulator can be used to dynamically adjust the focus of the light by creating phase curvature. Depending upon the scan angle along the axis, the phase modulator can correct for field curvature along one axis thereby enabling a wider scan angle to refocus onto a flat plane using adaptive optics 1307. Phase grating 1309 can operate at about 600 Hz and can redirect the laser in an instantaneous point and shoot fashion—it does not require continuous scanning through angles. The beam can be redirected along x-axis 1311 as it is moved along a y-axis by a tractor, and can be refocused to different z-positions 1313. The response time is limited by the liquid crystal elements themselves and some adjustment can improve the speed to about 500 Hz refresh rates.

To enhance the range of the phase grating beam steering which is typically only about 10 degrees for high efficiency steering about 75% power in the primary diffractive mode, discrete large aperture transparent polarization grating switches can be used to instantaneously switch the laser through discrete large angles if the laser light is polarized. This allows the laser to be steered over a wide field and with high precision along one or two dimensions. When combined with a phase grating modulator, a large field of regard can be achieved with precision control over the scan angle.

Non-mechanical steering module 1300 can be moved in a y-direction when mounted on a chassis that is part of a tractor. In this disclosure, a tractor is any vehicle that can move steering module 1300 in a y-axis direction. Tractor systems typically run at speeds of 1.5 msec to 2.5 msec. Assuming a 2 msec reprogramming time between laser shooting events, a tractor will move a linear distance of only 3 mm to 5 mm. During this time the laser can severely damage an unwanted plant with multiple laser firings. As long as the unwanted plant density is less than about 1 plant/cm$^2$ the laser steering system has enough time to be reconfigured to fire at the target of the next unwanted plant. With such a non-mechanical phased array beam steering module along the length of a tractor cultivator, a wide row of crops can be "weeded" in a single pass.

The one-dimensional modulator can only compensate for focal variation along one dimension. To enhance the effectiveness of the non-mechanical steering module, a cylindrical adaptive optics MEMS mirror element (shown as 1307 in FIG. 13) can be employed. Such a MEMS adaptive mirror can be made using a silicon-nitride gold sputtered membrane that is electrostatically actuated to produce a small change in curvature. Such MEMS structures, due to their small size, can be very vibration insensitive having resonant frequencies well above 1 kHz.

A lawn weeding system described herein includes an embodiment of an apparatus as described above. The lawn weeding system may also include a lawn mower. The lawn mower can be a hand or tractor-propelled lawn mower or a self-propelled motorized lawn mower (gasoline, diesel, electric, solar, or electric). If the lawn mower is hand-propelled it may include a power source to power the three-dimensional imager, the image processor, the at least one laser device, and the guidance system. If the lawn mower is tractor-propelled, it can, in some embodiments, generate power to energize at least one of the three-dimensional imager, the image processor, the at least one laser device, and the guidance system.

In some embodiments, the lawn mower can include cutting means. The cutting means can include, for example, a rotating reel of lateral blades, a rotating single blade, or a laser cutter (electro-optical). In some embodiments, the cutting means include electro-optical cutting means, such as a laser cutting apparatus that can utilize a plurality of rotating laser beams for cutting vegetation such as, for example, grass growing in a lawn. In some embodiments, it is contemplated that the at least one laser device configured to emit a laser beam having power sufficient to damage the unwanted plant can also be used to cut vegetation, such as grass, in a lawn. In one such embodiment, the laser device can distinguish between an unwanted plant (weed) and a wanted plant (grass lawn) and can both damage the unwanted plant and cut the wanted plant (mow the lawn). In this embodiment, the electro-optical cutting means and the laser beam can have sufficient power to both be able to damage an unwanted plant and also to cut vegetation.

Figure 14:
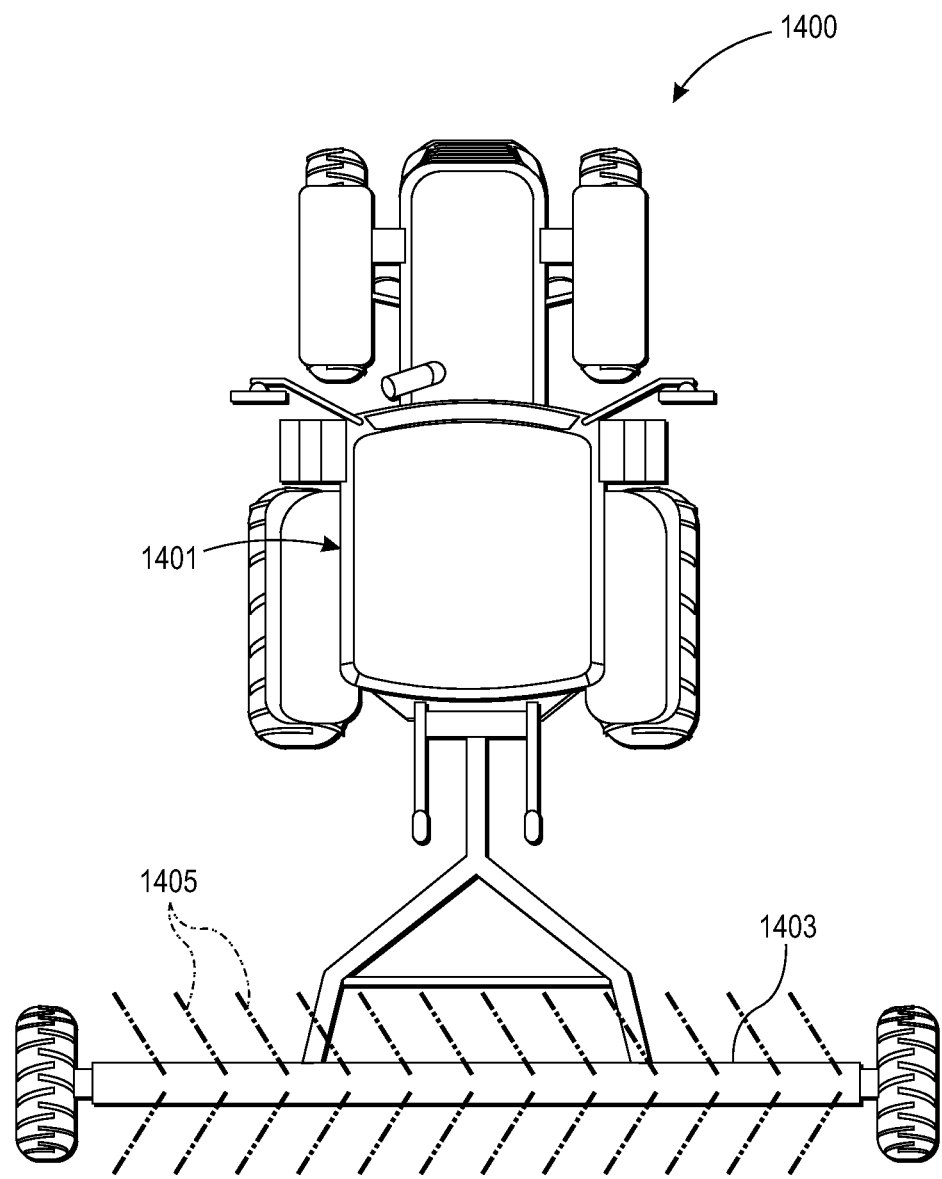
FIG. 14 is a schematic drawing of an embodiment of a chassis mounted with a laser weeding apparatus.

FIG. 14 is a schematic drawing of an embodiment of an apparatus that includes a laser weeding module. Apparatus 1400 includes tractor 1401 to which is attached trailer 1403. Trailer 1403 includes a three-dimensional imager, an array of laser devices and a laser beam controller. Apparatus 1400 also can include an image processor configured to distinguish between a wanted plant and an unwanted plant. Apparatus 1400 can be moved across an agricultural field or a lawn and can identify and locate unwanted plants. The array of laser devices on trailer 1403 can produce a plurality of laser beams 1405 that can be directed to one or more unwanted plants.

In another aspect, some embodiments of a method for removing unwanted plants include capturing plant images using a three-dimensional imager. Such processes and apparatuses are discussed above. Embodiments of the method also include distinguishing between a wanted plant and an unwanted plant after capturing plant images. Embodiments of the method also include directing a laser beam from at least one laser device towards the unwanted plant, and damaging the unwanted plant with the laser beam. Some embodiments of the method can also include a guidance system configured to direct at least one laser beam towards the unwanted plant. In other embodiments, the chassis can be moved across an agricultural field or lawn.

Figure 15:
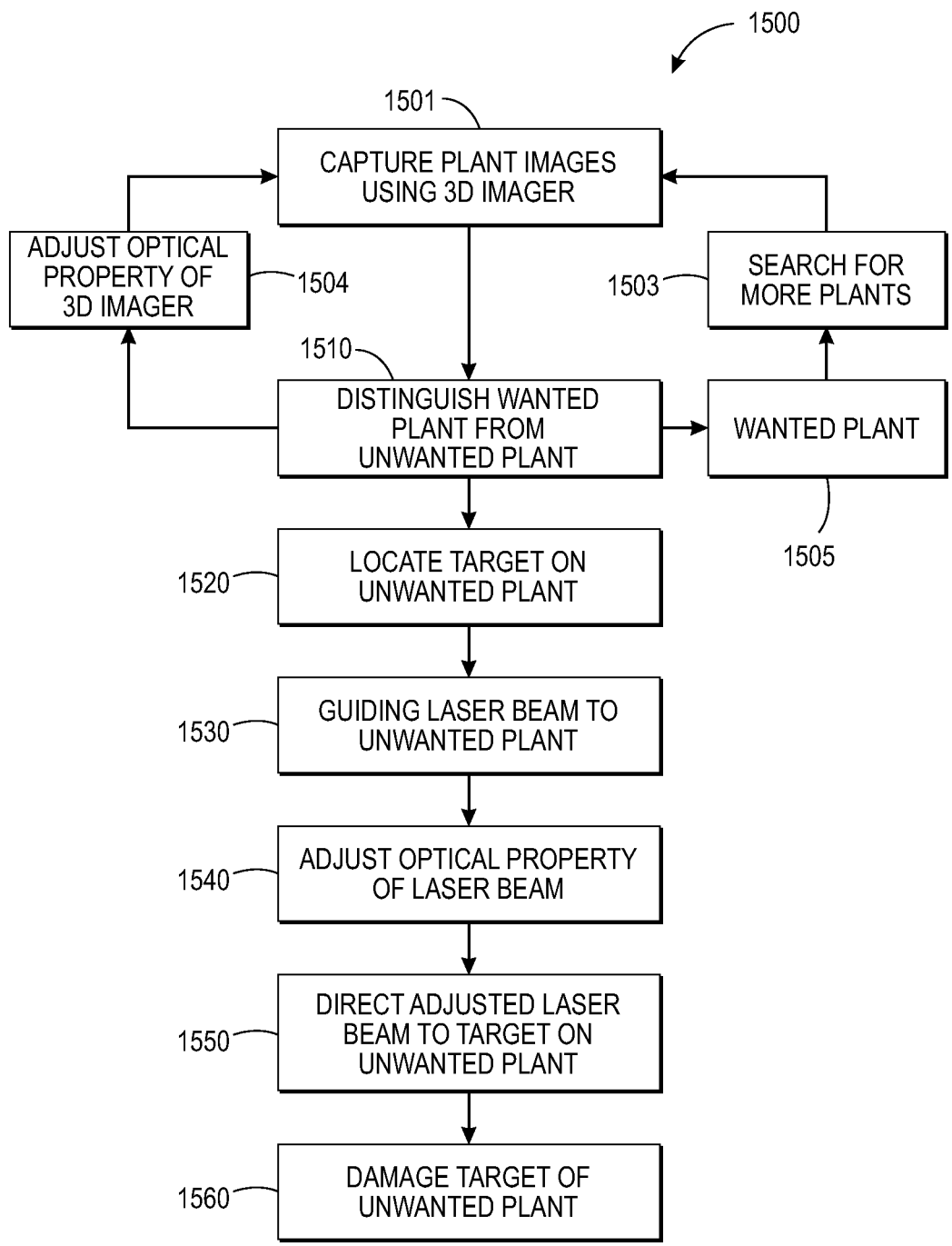
FIG. 15 is a flow diagram of an embodiment of a method.

An embodiment of disclosed methods is shown in flow diagram format in FIG. 15. Process 1500 includes capturing plant images using a three-dimensional imager as shown in step 1501. The captured plant images are used to distinguish a wanted plant from an unwanted plant as shown in step 1510. If the plant is a wanted plant 1505, the three-dimensional imager is configured to search for more plants as shown in step 1503. If the plant is an unwanted plant, a target can be located on the unwanted plant as shown in step 1520. If desired or necessary, optical properties of the three-dimensional imager can be adjusted to help distinguish between a wanted plant and an unwanted plant as shown in step 1504. If the plant is a desired or wanted plant, no further action from the apparatus is forthcoming. If the plant is an unwanted plant that needs to be damaged, destroyed, or removed, it is located as shown in step 1520. A guidance system is used to select and to focus at least one laser beam on the unwanted plant as shown in step 1530. Optics associated with the at least one laser beam can be adjusted (step 1540) and the adjusted laser beam can be directed to target of the unwanted plant as shown in step 1550. Finally, the unwanted plant can be damaged as shown in step 1560 and, hopefully dies and disintegrates.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. A method of removing unwanted plants comprising:
capturing plant images using a three-dimensional imager;
distinguishing between a wanted plant and an unwanted plant after capturing plant images;
locating a target on the unwanted plant;
guiding, with a non-mechanical phased array beam steering module, at least one laser device configured to emit at least one laser beam to the target of the unwanted plant, the non-mechanical phased array beam steering module is coupled to a cylindrical-shaped MEMS mirror adaptive optical element;
modulating a phase of the at least one laser beam;
redirecting, the phase modulated, at least one laser beam to the unwanted plant using a phase grating;
adjusting at least one of a depth of field, a width of field, or a focal length of the at least one laser beam;
directing the adjusted at least one laser beam to the target on the unwanted plant; and
damaging the target on the unwanted plant with the at least one laser beam.

2. A method of removing unwanted plants according to claim 1, further comprising mounting the three-dimensional imager and the at least one laser device on a chassis.

3. A method of removing unwanted plants according to claim 2, further comprising moving the chassis across an agricultural field or lawn.

4. The method of removing unwanted plants according to claim 3, further comprising cutting grass and killing the unwanted plants as the chassis moves across the agricultural lawn or field.

5. The method of removing unwanted plants according to claim 4, wherein cutting the grass comprises electro-optically cutting the grass and killing the unwanted plants as the chassis moves across the agricultural lawn or field.

6. The method of removing unwanted plants according to claim 1, wherein adjusting at least one of a depth of field, a width of field, or a focal length of the at least one laser beam comprises adjusting each of the depth of field, the width of field, or the focal length of the at least one laser beam.

7. The method of removing unwanted plants according to claim 1, further comprising adjusting a wavelength of the laser beam.

8. The method of removing unwanted plants according to claim 7, wherein the wavelength of the laser beam is from about 430 nm to about 475 nm or from about 650 nm to about 675 nm.

9. The method of removing unwanted plants according to claim 8, wherein adjusting the wavelength of the laser beam comprises adjusting the wavelength based on distinguishing a type of the unwanted plant.

10. The method of removing unwanted plants according to claim 1, further comprising dynamically adjusting a focus of the at least one laser beam by creating phase curvature.

\* \* \* \* \*